Figure 1:
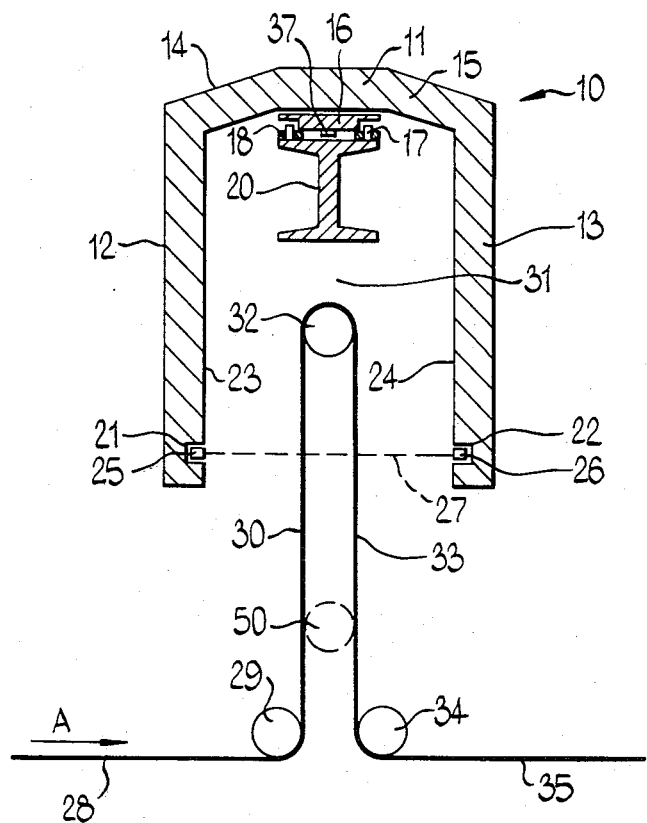

United States Patent [19]

Cameron

[11] 4,292,536
[45] Sep. 29, 1981

[54] RADIATION METHOD AND ASSEMBLY FOR ASSESSING WEB PARAMETERS

[75] Inventor: Ivor Cameron, Dumfries, Scotland

[73] Assignee: Imperial Chemical Industries Limited, London, England

[21] Appl. No.: 62,225

[22] Filed: Jul. 27, 1979

[30] Foreign Application Priority Data

Aug. 7, 1978 [GB] United Kingdom ............... 32466/78

[51] Int. Cl.³ ............................................. G01N 23/00
[52] U.S. Cl. .................................... 250/359; 250/360
[58] Field of Search ............... 250/338, 339, 340, 341, 250/358 R, 359, 360, 571

[56] References Cited

U.S. PATENT DOCUMENTS

| | | |
|---|---|---|
| 2,557,868 | 6/1951 | Fua et al. |
| 3,555,288 | 1/1971 | Morenius |
| 3,803,414 | 4/1974 | Van Horne et al. ........... 250/341 X |
| 3,860,820 | 1/1975 | Ryan ..................................... 250/360 |
| 3,875,417 | 4/1975 | Holben et al. |
| 3,879,607 | 4/1975 | Bjorklund ....................... 250/341 X |

FOREIGN PATENT DOCUMENTS 9238 of 1910 United Kingdom .

*Primary Examiner*—Davis L. Willis
*Attorney, Agent, or Firm*—Cushman, Darby & Cushman

[57] ABSTRACT

The invention relates to an assembly and method for assessing a radiation-sensitive web parameter, such as the thickness of a polymeric film, by passing a web inwardly along a first path and withdrawing the web along a substantially parallel second path between a radiation source (25) and detector (26) mounted on the respective limbs (12, 13) of a stirrup cradle (10), monitoring radiation transmitted through both thicknesses of the web, and, preferably, traversing the cradle across the web paths. The invention enables a constant spatial relationship to be maintained between the source and detector, thereby improving the accuracy of the measurement technique, and is particularly suitable for assessment of the thickness of polymeric packaging films.

7 Claims, 5 Drawing Figures

RADIATION METHOD AND ASSEMBLY FOR ASSESSING WEB PARAMETERS

This invention relates to an assembly and a method for assessing variations in a selected parameter of a moving web by monitoring radiation transmitted by the web. In particular it relates to equipment and techniques for measuring the thickness of a moving web, such as a paper web or a polymeric film.

Webs exhibiting variations in parameters such as thickness and profile across the width thereof are usually commercially unacceptable, and in recent years much attention has been devoted to techniques for rapidly scanning webs during production to assess the extent of such variations thereby enabling appropriate corrective adjustment of the running conditions to be effected. For example, radiation from a suitable source may be directed at a surface of the web, that portion of the radiation transmitted from the opposed surface of the web being sensed by an appropriate detector and converted into a signal indicative of a selected characteristic of the web. Typical of such systems is the beta ray gauge in which electrons from a radioactive source are passed into a web where some are absorbed and the rest transmitted to a detector. The amount of radiation absorbed depends on the web mass, but for materials of constant density this dependence can be transformed to thickness, and the detector can be calibrated to provide an appropriate output signal. Instruments of this type are well suited for continuous thickness measurements, in which case the source and detector are disposed so that they repeatedly traverse the web in unison.

Radiation emitted by the source is also absorbed by the ambient atmosphere between the source and detector and a small variation in the separation between source and detector can introduce a variation in absorption and a consequent variation in the output signal corresponding to a significant proportion of the film parameter being assessed. To achieve acceptable accuracy and reproducibility of measurement it is therefore important that variations in the length of the radiation path between source and detector should be minimized.

In practice it is customary to provide an "O-frame" comprising a generally rectangular stationary framework of I-section girders through which the web is fed in the longitudinal or machine direction in a plane substantially parallel to the longer girders of the frame, the source and detector being slideably mounted respectively on these longer girders. Webs of width of the order of 4 meters, or greater, may be involved, and desirably the separation between source and detector should not vary by more than about ±2 mm as the radiation gauge assembly traverses the web. Consequently, to achieve the requisite rigidity of structure the "O-frame" must be of relatively massive construction and is therefore both cumbersome and costly. Furthermore, a stationary frame assembly of this kind requires the provision of means for independently traversing the source and detector component along the respective I-girders—usually by means of a reversiblydriven endless belt or cable coupled to each component. Difficulty is therefore experienced, for example—by stretching of the belt or cable or by flexing of the supporting girders, in maintaining the source and detector in adequate register with each other throughout the traversing movement. Lateral displacement of the source and detector relative to each other in this way inevitably introduces errors into the measured value of the web characteristic being assessed.

Alternatively, the supporting framework may be of generally U-configuration, with a root portion from which extend two limbs in parallel spaced-apart relationship, the source and detector being located on the respective limbs, and the web being fed between the limbs in a plane normal to that embracing the limbs with a longitudinal edge of the web adjacent the root portion. To enable radiation from the source to detect defects on any part of the web surface the limbs of the framework must necessarily extend at least across the entire width of the web and are therefore subject to vibration and attendant errors in the detected signal. A framework of this kind is therefore generally unsuitable for scanning across the width of the web, and is invariably employed in a stationary mode with severe reduction in the utility of the assembly. Furthermore, a relatively large dead space is required alongside the web path into which the framework can be retracted to an inoperative position for maintenance, and the like.

We have now devised an improved assembly and method for scanning a web.

Accordingly, the invention provides an assembly for assessing variations in a radiation-sensitive parameter of a moving web by monitoring radiation transmitted by the web comprising a stirrup-like cradle having a root portion, and extending therefrom, a pair of confronting limbs relatively spaced apart and dimensioned to define a bight to accommodate a web introduced and withdrawn along a path between the free ends of the limbs and the root portion, a mounting for a source of radiation on a distal portion of one limb, a mounting on a distal portion of the other limb for a detector to monitor radiation emitted by the source across the bight, and means for supporting the cradle about the web path.

The invention also provides an assembly for assessing variations in a radiation-sensitive parameter across the width of a moving web by monitoring radiation transmitted by the web comprising a stirrup-like cradle having a root portion, and extending therefrom, a pair of confronting coplanar limbs relatively spaced apart to define a bight to accommodate a web introduced and withdrawn along a path between the free ends of the limbs and the root portion, a mounting for a source of radiation on a distal portion of one limb, a mounting on a distal portion of the other limb for a detector to monitor radiation emitted by the source across the bight, and means for reciprocating the cradle across the web path in a plane substantially normal to that embracing the limbs.

The invention further provides an assembly for assessing variations in a radiation-sensitive parameter across the width of a moving web by monitoring radiation transmitted by the web comprising an open-ended stirrup cradle having a root portion and, extending therefrom, a pair of spaced-apart confronting limbs, a mounting for a source of radiation on a distal portion of one limb, a mounting on a distal portion of the other limb for a detector for monitoring radiation emitted by said source, guide means for directing a web inwardly between the distal portions of the limbs towards said root portion, reversal means for returning the web outwardly from said root portion between the distal portions of the limbs, and means for traversing the cradle across the width of the web.

The invention still further provides a method of assessing a radiation-sensitive parameter of a moving web comprising directing a beam of radiation from a source to a detector, feeding a web through the beam of radiation along a first path, reversing the direction of travel of the web, returning the web through the beam of radiation along a second path substantially parallel to said first path, monitoring the radiation received at the detector by transmission through the web travelling along both web paths, and, preferably, traversing the beam of radiation and the detector across the width of the web.

The stirrup cradle provides a rigid bifurcate framework having a root portion and a pair of limbs extending therefrom in spaced-apart relationship to provide support for the source and detector respectively, each of the limbs having one end thereof securely attached to the root portion and the ends of the limbs remote from the root portion, the distal ends, being separated from each other by a gap to permit passage of the web therethrough. Conveniently, the stirrup cradle is of generally U-configuration, although the operating technique of the invention enables the limbs thereof to be truncated to yield a cradle of generally C-configuration, thereby immensely increasing the rigidity of the cradle and reducing the incidence of errors caused by displacement of the source relative to the detector. Suitably the cradle is in the form of a casting, for example—of an aluminium alloy offering a combination of low mass, high strength, and good rigidity.

A mounting is provided on a distal portion of each limb for the source and detector respectively, and may comprise a site to which the source or detector is secured by conventional fastening means, or may include an adaptation of the limb portion to receive and releasably retain the source or detector. The respective mountings are preferably located at or near the free ends of the limbs remote from the root portion, but may be sited at any position along the limbs which permits the web to pass inwardly between source and detector towards the root portion of the stirrup cradle and, after reversal, to return outwardly in the opposite direction. The mountings should be positioned such that a beam of radiation emanating from the source is received by the detector, and preferably so that the beam of radiation is directed along a path substantially normal to the plane of the web.

The cradle is disposed relative to the web path on any suitable support member such as a relatively rigid single rail or girder, conveniently of I-section.

Preferably, the support member comprises a track on which the cradle can traverse the web path. Conveniently the cradle is mounted on a carriage slideably supported on the track—for example, on wheels or on slide or roller bearings. In a preferred embodiment the support member and slide carriage are positioned within the bight of the cradle, the carriage engaging the root portion of the cradle, although it will be appreciated that one or more support members may be alternatively positioned, as desired, externally and/or internally of the cradle.

Traversing of the cradle across the web path is conveniently effected by conventional means, such as an endless cable or belt attached to the carriage and supported on a pulley assembly coupled to a prime mover such as an electric motor through a reversible switching assembly to enable the carriage and cradle to reciprocate along the track. Alternatively the carriage assembly may be designed to float on the track under the influence of an electrical linear induction motor thereby enabling relatively high traversing speeds to be achieved. Although the cradle preferably traverses the entire width of the web, the traversing means may, if desired, be adjusted so that the system either scans only a selected portion of the web width, or remains stationary to monitor a narrow path in the machine direction of the web.

Guide means for directing the web inwardly between the source and detector mountings conveniently comprises one or more guide bars or rollers for diverting the web from its normal path into the bight of the cradle The reversal means for returning the web outwardly from the cradle is locatable within the bight and suitably comprises a rigid turner bar, rotatable roller, perforated air bar, or the like, around which the web is fed. If desired, the reversal means may be releasably mounted for displacement to a service position externally of the bight thereby enabling the web path to by-pass the cradle if required—for example, during preliminary threading of the web along the web production line or to facilitate servicing and maintenance of the equipment.

To reduce vibration of the web in the bight, thereby increasing the accuracy of the signal received at the detector, a stabilizing member, for example a bar or roller, may be introduced between the web guide and reversal means for engagement with one or preferably both of the inwardly and outwardly directed portions of the web.

The radiation source for mounting on one of the limbs of the cradle is of conventional type—for example, infra-red, ultra-violet or beta ray, and the detector for mounting on the opposed limb should be compatible with the source.

The assembly of the invention is mechanically simple, and therefore relatively inexpensive and easily maintained, while providing a rigid mounting for the source and detector enabling a fixed path length to be maintained therebetween, precluding displacement, including tilting, of the source relative to the detector in any direction, and eliminating alignment problems by ensuring that both source and detector traverse the web width in perfect synchronisation on a unitary mounting. The simple design of the cradle requires a minimal supporting structure and enables a web in the course of production to be intoduced to and withdrawn from the assembly "on the run" without interruption of the production schedule. Additionally, positioning of the cradle in an inverted configuration with the limbs extending upwardly ensures that the gauge assembly can be positioned entirely below the web thereby eliminating possible contamination of the web by debris falling from the assembly onto the web surface. Furthermore, arrangement of the cradle so that the detector monitors radiation transmitted through two thicknesses of web doubles sensitivity and ensures that the assembly in effect performs a limited instantaneous integration of the value of the parameter being assessed, and therefore is particularly suited to the assessment of thin film parameters. Digital recordal of the instantaneous position of the cradle relative to the web width is also facilitated by the assembly of the invention.

Webs suitable for assessment by the techniques of the present invention include paper, paperboard, cellulosic films, polymeric films, and laminates thereof. Typical polymeric films include oriented, particularly biaxially oriented, films formed in conventional manner from polyesters such as polyethylene terephthalate and polyethylene-1,2-diphenoxyethane-4,4'-dicarboxylate, from polymers and copolymers of 1-olefins such as ethylene, propylene, butene-1, and 4-methylpentene-1, and particularly from a high molecular weight stereoregular predominantly crystalline polymer of propylene, either in the form of a homopolymer or copolymerised with minor quantities (e.g. up to 15% by weight of the copolymer) of at least one other unsaturated monomer, such as ethylene. The technique is also applicable to a coextruded multiplelayer film having a polypropylene substrate with a coextruded layer comprising a propylene-butene-1 copolymer on at least one surface thereof.

Webs suitable for assessment according to the present invention may vary in thickness over a wide range but will usually have a thickness of from 2 to 150 microns. Packaging films are generally within a thickness range of from 5 to 50 microns.

The invention is illustrated by reference to the accompanying drawings in which

Figure 2:
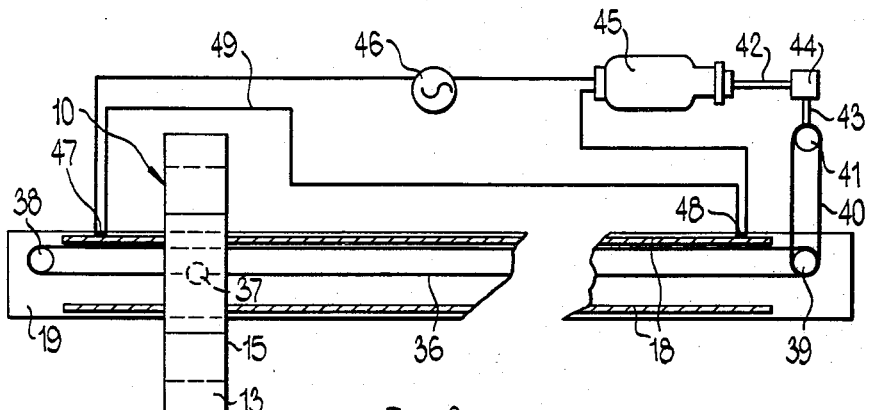
Figure 3:
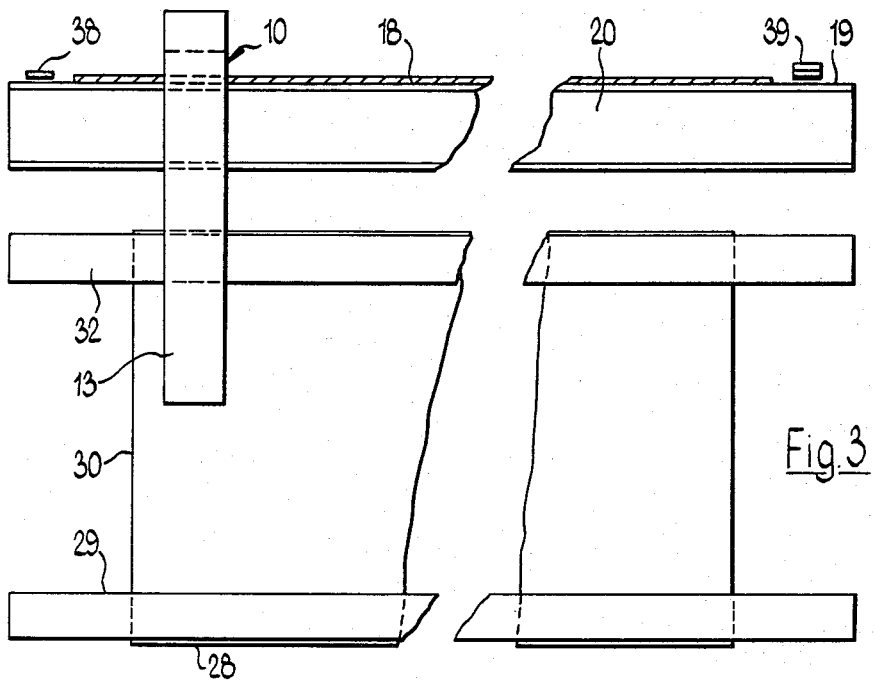
Figure 4:
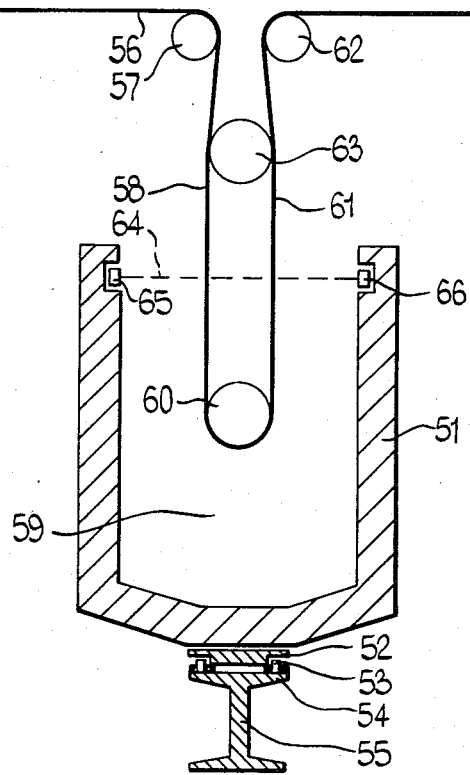
Figure 5:
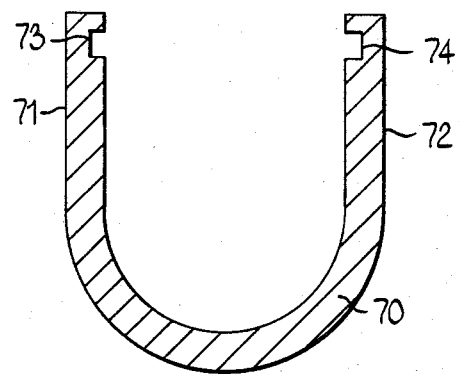

FIG. 1 is a schematic end elevation, not to scale, of a gauge assembly with a cradle disposed in the operative position about a web path, FIG. 2 is a schematic plan view of the gauge assembly illustrating a cradle traversing mechanism, FIG. 3 is a schematic side elevation of the assembly shown in FIG. 2, illustrating web guide and reversal rolls, FIG. 4 is a schematic end elevation illustrating a cradle in the inverted position and including a web stabilising roll, and FIG. 5 is a schematic end elevation of an alternative form of cradle.

Referring to FIGS. 1 to 3 of the drawings a cradle, generally designated 10, having a root portion 11 and limbs 12, 13 extending therefrom via intermediate shoulder portions 14, 15 is secured to a carriage 16 mounted on wheels 17 running in channels 18 extending lengthwise along the uppermost flange 19 of a supporting I-section girder 20.

Recesses 21, 22 are provided in the confronting faces 23, 24 of the distal portions of limbs 12, 13 to accept respectively a radiation source 25 and an associated detector 26 responsive to radiation beamed from the source along a path 27.

A web, such as a polymeric film, 28 moving in the direction of arrow A is diverted around a guide roll 29 and directed along a path 30 through radiation beam 27 and into the loop or bight 31 defined by cradle 10. A reversal roll 32 positioned in the bight returns the web along a second path 33 through, and substantially normal to, the radiation beam, and a second guide roll 34 directs the web along path 35 to a wind-up or further processing station (not shown).

Referring particularly to FIG. 2 of the drawings, cradle 10 is traversed across the web paths, lengthwise along supporting girder 20, in guide channels 18, by means of an endless toothed belt 36 attached to the root portion of cradle 10 by coupling 37 and riding on pulleys 38 and 39 rotatably mounted towards opposed ends of the top flange 19 of the supporting girder. Double pulley 39 is driven through endless belt 40 by pulley 41 coupled through shafts 42, 43 and gear box 44 to an electric motor 45 supplied from an alternating current source 46. Limit switches 47, 48 in the electrical supply leads 49 to motor 45 are positioned respectively at opposed ends of flange 19 for engagement with an abutment (not shown) on cradle 10 to reverse the polarity of motor 45 thereby ensuring that the cradle reciprocates along the supporting girder and enabling the radiation beam to scan repeatedly across the width of the web.

Radiation from source 25 (FIG. 1) transmitted through both thicknesses of the web 30, 33 as cradle 10 traverses the web path is monitored by detector 26 and a signal therefrom transmitted to a receiving station (not shown) where the signal can be recorded and/or utilized to initiate corrective measures to alter the web parameter, e.g. thickness, being assessed.

As shown in FIG. 1, reversal roll 32 is retractable to a service position 50 (broken lines) which enables the web to by-pass cradle 10 without interruption of the web forming or treating process. Alternatively, the reversal roll may be retained in the operative position 32, and cradle 10 retracted from around the web path by raising supporting girder 20.

FIG. 4 illustrates an alternative arrangement in which a cradle 51 is supported in an inverted configuration on a carriage 52 running in channels 53 on the uppermost flange 54 of an I-section girder 55. A moving web 56 is diverted by guide roll 57 along a path 58 into bight 59, returned around reversal roll 60 along a second path 61 and diverted back into the production path by a second guide roll 62. A stabilising roll 63 is located between the first and second web paths through the bight to maintain the web in a flat condition as it passes through radiation beam 64 directed from source 65 to detector 66. The separation between guide rolls 57 and 62 is less than the diameter of stablilising roll 63 to maintain the web taut in the radiation beam. Preferably the diameter of stabilising roll 63 marginally exceeds that of reversal roll 60.

FIG. 5 illustrates an alternative cradle, generally of U-configuration with a root portion 70 and extending therefrom a pair of opposed parallel limbs 71, 72 recessed respectively at 73, 74 to receive a radiation source and detector.

Although the girder support has been illustrated in engagement with the root portion of the cradle it will be appreciated that the support means may be alternatively positioned, if desired, for example—with a supporting member in engagement with either or both of the cradle limbs either internally or externally of the cradle.

Likewise, although the cradle has been illustrated with the limbs extending vertically, the cradle may be alternatively positioned—with the limbs extending horizontally or at an angle inclined thereto.

I claim:

1. An assembly for assessing variations in a radiation-sensitive parameter of a moving web by monitoring radiation transmitted by the web comprising a stirrup-like cradle having a root portion, and extending therefrom, a pair of confronting limbs relatively spaced apart and dimensioned to define a bight to accommodate a web introduced and withdrawn along a path between the free ends of the limbs and the root portion, a mounting for a source of radiation on a distal portion of one limb, a mounting on a distal portion of the other limb for a detector to monitor radiation emitted by the source across the bight, and means for supporting the cradle about the web path.

2. An assembly according to claim 1 comprising means for reciprocating the cradle across the web path in a plane substantially normal to that embracing the limbs.

3. An assembly according to claim 1 comprising guide means for directing a web inwardly between the distal portions of the limbs towards said root portion, and reversal means for returning the web outwardly from said root portion between the distal portions of the limbs.

4. An assembly according to claim 1 wherein the supporting means is positioned within the bight of the cradle.

5. An assembly according to claim 1 comprising a web stabilizing member.

6. An assembly according to claim 1 wherein the cradle is mounted in an inverted position with the limbs extending upwardly.

7. An assembly according to claim 1 comprising an infra-red radiation source mounted on a distal portion of one limb and a detector, receptive to radiation emitted by said source, mounted on a distal portion of the other limb.

* * * * *